United States Patent
Colvin et al.

(10) Patent No.: US 6,716,243 B1
(45) Date of Patent: Apr. 6, 2004

(54) CONCENTRIC PASSIVE KNOTLESS SUTURE TERMINATOR

(75) Inventors: Stephen B. Colvin, New York, NY (US); Eugene Grossi, New York, NY (US); Alan Katz, Freeport, NY (US)

(73) Assignee: Quickie, Inc., New York, NY (US)

( * ) Notice: Subject to any disclaimer, the term of this patent is extended or adjusted under 35 U.S.C. 154(b) by 642 days.

(21) Appl. No.: 09/660,745

(22) Filed: Sep. 13, 2000

(51) Int. Cl.$^7$ ................................................. A61F 2/24
(52) U.S. Cl. ........................ 623/2.4; 606/2.32; 623/2.41
(58) Field of Search ................................. 606/213, 215, 606/232; 623/2.36, 2.38, 2.39, 2.4, 2.41

(56) References Cited

U.S. PATENT DOCUMENTS

| | | | |
|---|---|---|---|
| 4,185,636 A | * 1/1980 | Gabbay et al. | 606/148 |
| 4,235,177 A | 11/1980 | Arbuckle | |
| 4,291,698 A | 9/1981 | Fuchs et al. | |
| 4,986,023 A | * 1/1991 | Bucholz | 43/44.87 |
| 5,041,130 A | * 8/1991 | Cosgrove et al. | 623/2.11 |
| 5,188,638 A | 2/1993 | Tzakis | |
| 5,474,572 A | 12/1995 | Hayhurst | |
| 5,492,343 A | * 2/1996 | Smith et al. | 277/638 |
| 5,626,590 A | 5/1997 | Wilk | |
| 5,645,553 A | 7/1997 | Kolesa et al. | |
| 5,669,919 A | * 9/1997 | Sanders et al. | 606/148 |
| 5,681,351 A | * 10/1997 | Jamiolkowski et al. | 606/232 |
| 5,702,397 A | * 12/1997 | Goble et al. | 606/72 |
| 5,766,240 A | * 6/1998 | Johnson | 623/2.39 |
| 5,776,188 A | * 7/1998 | Shepherd et al. | 623/2.38 |
| 5,899,921 A | 5/1999 | Caspari et al. | |
| 5,919,208 A | 7/1999 | Valenti | |
| 5,951,590 A | 9/1999 | Goldfarb | |
| 5,980,558 A | 11/1999 | Wiley | |
| 6,017,304 A | 1/2000 | Vierra et al. | |
| 6,066,160 A | * 5/2000 | Colvin et al. | 606/232 |
| 6,527,794 B1 | * 3/2003 | McDevitt et al. | 606/232 |
| 6,558,416 B2 | * 5/2003 | Cosgrove et al. | 623/2.11 |
| 2002/0058994 A1 | * 5/2002 | Hill et al. | 623/2.11 |

* cited by examiner

*Primary Examiner*—Henry Bennett
*Assistant Examiner*—Kathryn Odland
(74) *Attorney, Agent, or Firm*—Greenberg Traurig LLP; Todd S. Sharinn

(57) ABSTRACT

The present invention provides a suture-terminating device comprising a central body having at least one surface, a plurality of flanges extending radially from the surface and defining at least one grove therebetween, each flange having at least one aperture axially aligned and spaced away from the base wall, at least one removable member disposed within each aperture, and at least one spring disposed adjacently to the surface and maintained in its activated state by contact with a removable member disposed within the aperture. The grove has a base wall and at least one sidewall. The spring, while in its active state, is positioned adjacent to and spaced from the base wall, defining a gap of sufficient size to permit the passage of at least one suture therethrough. The surgeon actuates the device by withdrawing the removable member from the aperture, thus permitting the spring to return to its resting state within the grove. The spring and the base and side walls cooperate to restrict the suture's movement through the gap.

31 Claims, 7 Drawing Sheets

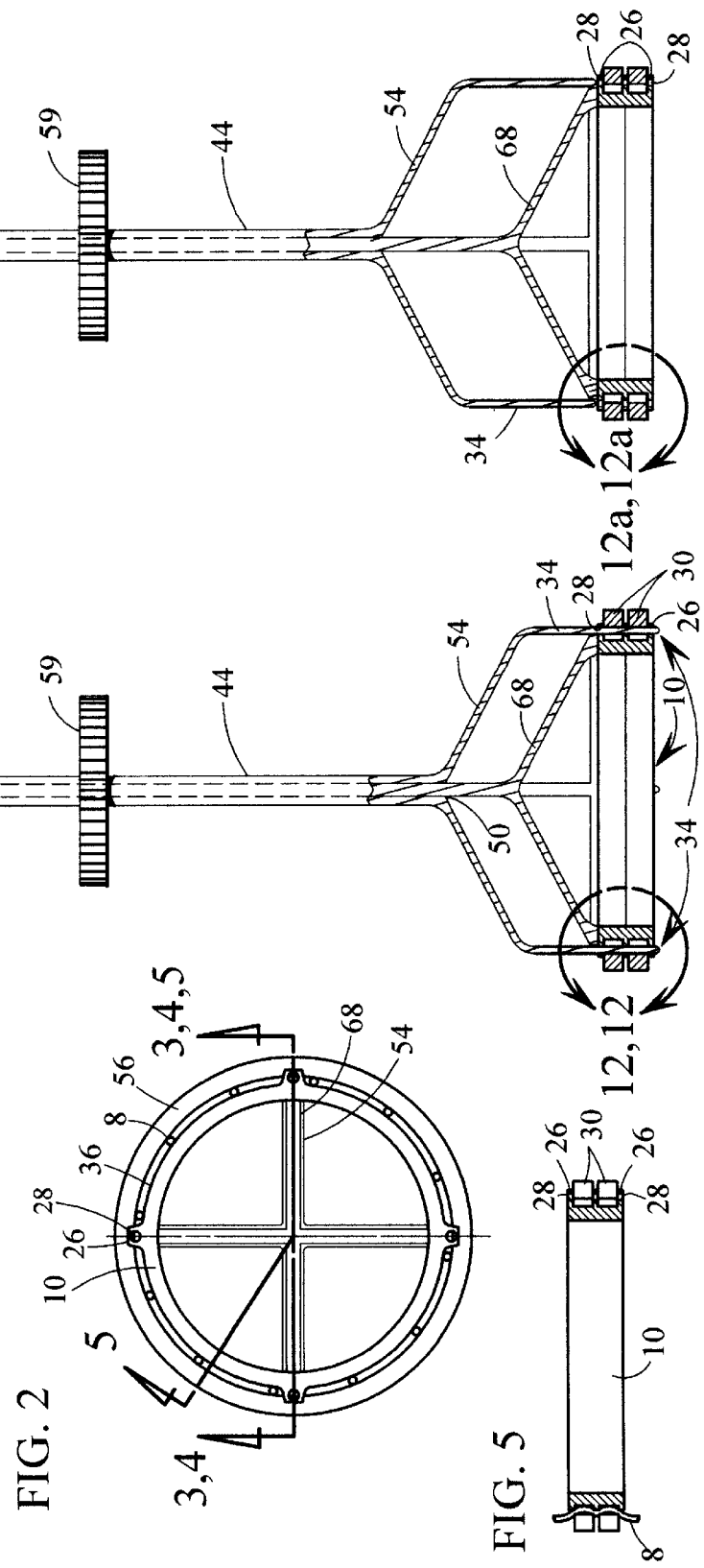

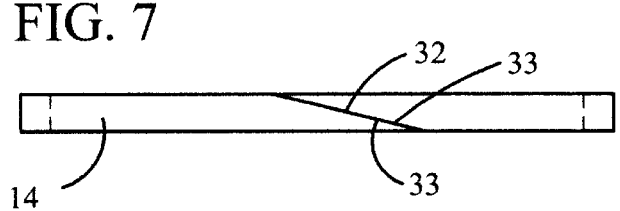
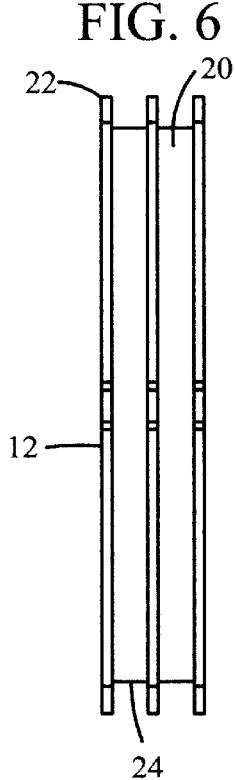
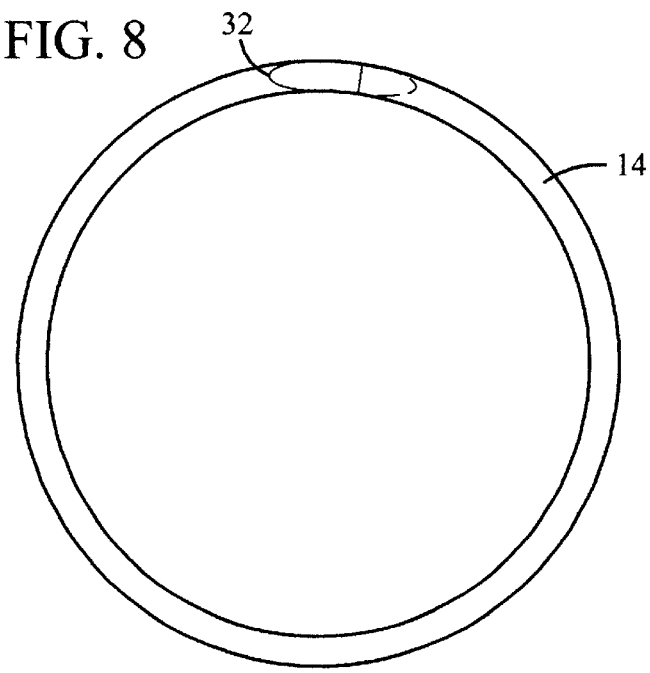
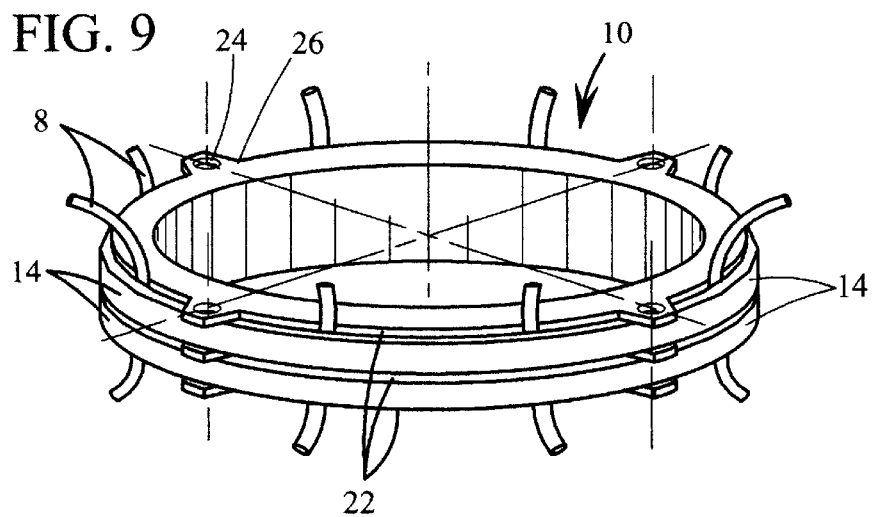

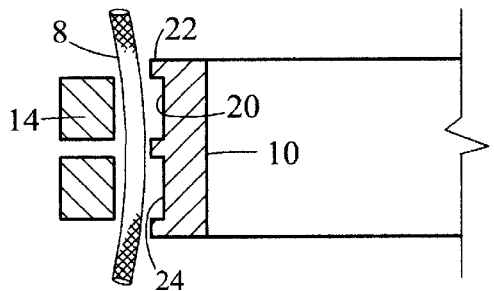
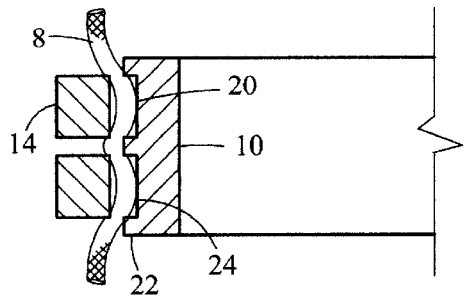
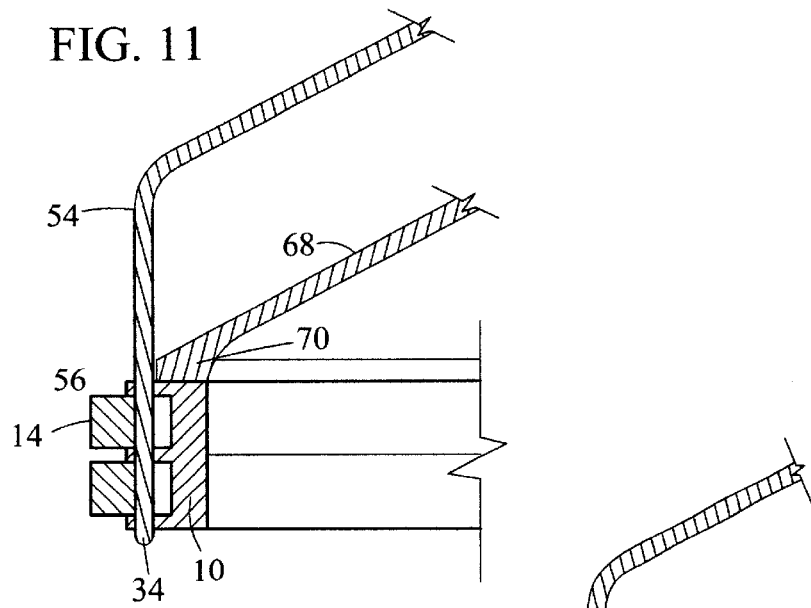
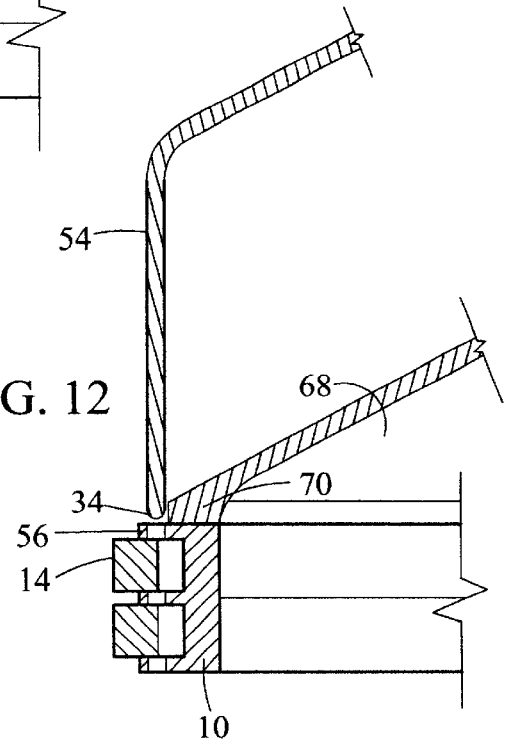

CONCENTRIC PASSIVE KNOTLESS SUTURE TERMINATOR

FIELD OF THE INVENTION

The instant invention relates to apparatus and systems for use in securing prosthetics to native tissue or tissue to native tissue in medical procedures. More particularly, this invention relates to apparatus and systems which facilitate securing the ends of standard sutures which can be used to secure tissues to native tissue or prosthetic devices to native tissue without requiring activation of the device.

BACKGROUND OF THE INVENTION

Suturing is an integral part of surgery. It is used to hold tissues together or to secure prosthetics (including but not limited to, heart valve prosthetics, annuloplasty rings, vascular grafts, and orthopedic implants) to native tissue. Sutures have conventionally been used to fasten such implants. The suture material is passed through the native tissue and then through part of the prosthetic or adjacent native tissue. The two are then drawn and secured together by tying a knot on the end of the suture.

By way of example, heart valve replacements and prostheses have been used for many years and many improvements in both the functionality and ease of implantation have been made thereon. More precisely, during conventional heart valve replacement surgery, sutures are placed in the native annulus after removal of a damaged native valve. Often small pledgets are threaded on the sutures to buttress their contact with the native tissue. The suture is then inserted through the suture ring of the replacement heart valve. Knots are then tied on the sutures to secure the replacement heart valve to the native heart annulus in its desired position such that there will be no leakage around the replacement heart valve.

When it is recognized that each of the completed knots used to secure the replacement heart valve to the native annulus is actually composed of six or more individual knots, it will be appreciated that this task would take a surgeon a significant amount of time to secure the replacement heart valve into position. Further, with the increased level of difficulty associated with this process, comes an increase in the likelihood of error by the surgeon. In addition, since the incision must be larger and the procedure requires greater time, the patient is exposed to collateral risk factors (which include, but are not limited to, an increased incidence of infection, hypothermia, and fluid loss).

Traditionally, the conventional prosthetic attachment procedure has required the surgeon to possess great dexterity and to be in close proximity to the knot. Emerging minimally invasive surgical techniques add an extra level of difficulty to this task since the incisions associated with such methods are generally much smaller than in conventional surgery. As a result, surgeons are required to spend more time tying off the sutures, or in some cases are required to stretch the incision in order to complete the task. By requiring the surgeon to make larger incisions to gain access to tie these knots, the advantages commonly associated with these minimally invasive surgical procedures, are quicker healing, less disruption to surrounding tissues and less likelihood of infection, are jeopardized.

Sensitive to these new demands, methods and apparatus for implanting heart valve replacement devices under minimally invasive conditions have been developed. Examples of such apparatus and methods for implanting heart valve replacement devices have been disclosed in U.S. Pat. Nos. 4,655,773; 4,364,126; 4,204,283; 3,898,999; 3,996,623; 3,859,668; 3,534,411; and 5,776,188. Indeed, apparatus and methods have been disclosed that avoid the use of sutures altogether. For example, U.S. Pat. No. 3,143,742 discloses spacing curved pins along the circumference of the apparatus to pierce the tissue of the native annulus of the heart at the desired attachment point. Unfortunately, due to vagaries in the native tissue, good coaptation along a geometrically perfect surface is not always possible.

Novel technologies have been deployed for the purpose of sewing heart valve subcomponents together. U.S. Pat. Nos. 5,071,431; 4,863,460; and 4,743,253 each use a ductile or deformable locking ring as a means to bind the various subcomponents of the heart valve device. However, the aforementioned approaches do not avoid the securing of the implant to the native tissue without the use of traditional suturing methods.

Recently, medical instruments have been developed which permit surgeons to manipulate sutures through a small opening. However, these instruments, which provide an extension between the surgeon's hands and the suture, are cumbersome, thus impeding the surgeon's ability to appropriately place the suture knot.

In response to this problem, surgeons have sought alternatives to conventional knot-tying techniques. Various sutures and suture-terminating devices have been disclosed. The most frequently disclosed among these alternatives is the use of surgical clips, which are designed to replace suture knots.

Examples of surgical clips to terminate sutures have been disclosed in a number of patents including U.S. Pat. Nos. 3,976,079; 5,282,832; 5,078,731; 5,474,572; 5,171,251; and 5,409,499. In general, these devices contain locking mechanisms that require the surgeon to deform the device on the suture's path and entrap the suture material in the clip. The suture is fixed in a single location and thus the necessity of tying a knot on the suture is avoided. These devices are problematic because they require actuation and, more importantly, pinpoint accuracy by the surgeon since they are not adjustable.

Still other configurations of surgical clips are disclosed in U.S. Pat. Nos. 5,078,731; 5,474,572; 5,171,251; and 5,409,499. These clips are also actuated by the surgeon's deformation of the device. The locking mechanisms in these devices are incorporated into the device's body. However, lateral access is required in order to actuate these clips. This cumbersome configuration makes them difficult, if not impossible, to incorporate into prosthetics. Further, these clips also lock the suture into a single position once actuated. This abridges the surgeon's ability to further adjust the tension on the suture, thus requiring the surgeon to remove the suture and repeat the process in order to achieve, when necessary, better coaptation of the tissue by the suture.

Still other surgical clips are disclosed in U.S. Pat. Nos. 3,976,079 and 5,282,832. Both of these clips incorporate an additional mating component (retaining clip 96 and retainer 120, respectively), which when attached to the clip locks the suture in place. However, the use of small loose parts is highly undesirable since it is easy to drop and lose such pieces through a minimally invasive incision. Indeed, if this were to occur, for example, inside a patient's heart, the potential for an arterial embolus and patient injury would greatly increase. Again, these clips, like all the aforementioned clips, lock the suture into a single position, which, as discussed above, has many disadvantages.

Additionally, modifications of sutures and surgical ties have been disclosed in U.S. Pat. Nos. 5,123,913 and 4,955,913. The methods presented in these patents include the use of a modified suture or surgical tie having serrations or ridges on the suture's or tie's bodice, which when mated with the appropriate closure device, the suture or tie is allowed to be freely advanced towards closure and cannot slide backwards. This allows the surgeon to incrementally increase the tension on the suture or tie without the need to tie a knot. These modified sutures/ties are not suitable for most surgical applications, since they can not be passed through tissue or prosthetics like a standard suture. In addition, neither of these devices affords the surgeon with the opportunity for precise tightening of the suture or tie since the serrations or ridges are incremental. Further, U.S. Pat. No. 5,123,913 discloses a modified suture-terminating with a loop member which is designed to mate with the serrations along the length of the suture. While this will function as a surgical suture, the loop member increases the length of the device, making it unsuitable for certain surgical applications, such as securing a heart valve inside the heart. Additionally, these inventions are not compatible with standard sutures.

U.S. Pat. No. 5,776,188 discloses three pertinent apparatus for securing a suture without a knot to a heart valve sewing ring. In the first apparatus, plugs 192 (as illustrated in FIG. 5) have been credited as devices that help secure the suture in place. This is similar to the suture clip methodology that was discussed above. The drawbacks associated with these plugs are that they: (1) do not eliminate the need for a knot to be tied, (2) do not allow the tension to be incrementally adjusted on the suture, (3) have the potential to dislodge causing patient injury, and (4) may be difficult to position in a minimally invasive cardiac procedure.

The second apparatus provided by U.S. Pat. No. 5,776,188 incorporates the use of ball 248 and chamfered slot 242. As illustrated in FIG. 7, the ball and slot cooperate to effectuate the securing of sutures to a heart valve sewing ring without the necessity of a knot. While this embodiment may fasten a suture to the valve sewing ring, it is undesirable to surgeons for a number of reasons. First, this embodiment utilizes a free-floating piece (ball 248) which has the potential to dislodge or jam. Consistent with the concerns raised above, relating to U.S. Pat. Nos. 3,976,079 and 5,282,832, if the ball were to dislodge from the device, it could harm the patient. Further, although this embodiment may engage the suture, the rounded nature of the ball will minimize the field of contact and the resulting integrity of the grip thereon. This greatly reduces suitability for such a device since most surgical procedures require a strong and permanent grip.

The final apparatus disclosed within U.S. Pat. No. 5,776,188 relies on pressure generated by the single spring 252 to secure the suture. More particularly, spring 252, which is a small separate piece attached to the device, impedes the suture's movement by trapping it. Therefore, the stronger the spring used, the more pressure it applies to the suture and the more reliable its grip will be. However, as the pressure increases the surgeon's ability to adjust or fine tune the tension applied to the suture is hampered. In addition, the strength of the grip is directly dependent upon the spring's stamina and strength. Further, consistent with the above discussion relating to the previous apparatus, spring 252 is not captured within the body of the device; accordingly, it is capable of breaking free from the device which could cause patient injury.

In addition to surgical clips, a number of suture anchoring devices have been disclosed. These devices restrict the suture's movement by subjecting the suture to frictional forces generated through a serpentine configuration of the suture's path through the device. Examples of such devices are disclosed in U.S. Pat. Nos. RE 36,289, 5,630,824, 5,514,159 and 5,376,101. Each of these devices anchor the sutures to tissue and/or prosthesis through the cooperation of multiple pieces. Like the devices disclosed in U.S. Pat. No. 5,776,188, if one of the pieces were to dislodge from the device, the patient could suffer. Although the present invention relies on the cooperation of two pieces, the pieces are formed in a tongue and groove-like configuration which prevents accidental separation and dislodging, and the deleterious effects that such an accidental separation could precipitate.

As will be more fully appreciated below, none of the aforementioned devices offer the ease and versatility for terminating sutures and thus securely locking tissues and/or prosthetics in place, as the instant invention. Indeed, the instant invention provides a means for securing tissues to native tissues and prosthetic implants to native tissue; the benefits of which may be most appreciated in operations where minimally invasive procedures are utilized.

The apparatus and systems disclosed herein obviate the need for manually tying knots, a procedure which typically requires the surgeon to manipulate his hands in tight proximity of the tissue being secured. This invention may be used as a freestanding device or may be incorporated into prosthetic implants such as heart valves, annuloplasty rings, orthopedic implants or the like, all of that require securing to native tissues.

Moreover, the devices of the instant invention are applicable to all instances of operative procedures where the surgeon needs to secure tissue with a suture, but has limited access for her/his hands to tie a knot. In instances of using sutures to stop bleeding or securing tissues or implants in minimally invasive procedures, the devices of the instant invention will facilitate the procedure by eliminating the time and physical exposure required to manually tie knots to terminate the suture. The present invention's advantages of enhanced tissue securing with minimal surgical exposure, decreased implementation time, and enhanced reliability are accentuated when compared to existing related technology.

SUMMARY OF THE INVENTION

Therefore, it is an object of the present invention to provide a suture-terminating device that is mechanically stable, and capable of securing prosthetics-to-native-tissue or tissue-to-nativetissue in medical procedures.

It is a further object of the present invention to provide a suture-terminating device that may be used as a freestanding device or may be incorporated into prosthetic implants such as heart valves, annuloplasty rings, orthopedic implants or the like.

It is still a further object of the present invention to provide a suture-terminating device that is particularly useful in minimally invasive surgical procedures.

It is still a further object of the present invention to provide a suture-terminating device that is easy to manufacture.

The present invention is directed to an apparatus and systems for use in terminating sutures. This invention can be used in a freestanding manner to terminate a suture which holds tissue together or it can be incorporated into a prosthetic in order to hold the prosthetic to the tissue. The present invention terminates the ends of standard sutures without knots and without the need for manual proximity, thus facilitating, among other things, minimally invasive surgical procedures.

One preferred embodiment of the present invention comprises a central body having at least two flanges running latitudinally around the circumference of its outer surface. While the central body will, under most circumstances, exist as a single unit, it is envisioned that under certain circumstances (e.g. when used in connection with certain pre-existing prosthetic devices), the central body will be constructed of at least two sections, which, once coupled, exists as a single unit, through the coaptation of the springs and with the central body.

Suture termination is accomplished through the cooperation of the central body with at least one split ring tension spring. Prior to actuation, the spring is maintained in its expanded state by removable members that are inserted between the spring and the central body through orifices on tabs that are located on the flanges. Once actuated, the spring contracts to rest tightly on the outer surface of the central body within the groove formed by the flanges.

Another preferred embodiment of the present invention comprises a central body having at least two flanges running latitudinally around the circumference of its inner surface. Suture termination is accomplished, through the cooperation of the central body with at least one split ring compression spring housed within the central body. Prior to actuation, the spring is maintained in its compressed state by removable members that are inserted between the spring and the central body through orifices on tabs that are located on the flanges. Once actuated, the spring expands to rest tightly on the inner surface of the central body within the groove formed by the flanges.

In either of the above referenced embodiments, the removable members maintain sufficient space between the outer surface of the central body and the spring to ensure the easy passage of a suture. Prior to actuation, the surgeon threads the sutures through the gap between the spring and central body. Subsequent to the passage of all necessary sutures through the suture-terminating device and once the surgeon is satisfied with the final position of the sutures, the removable members are withdrawn. The coaptation of the spring with the central body generates sufficient force on any sutures traversing the central body through the gap to restrict movement. Depending upon the desired result, the spring may be manufactured with sufficient force as to impede any movement of the suture.

Prior to actuation, removable members maintain sufficient space between the inner surface of the central body and the outer surface of the spring to ensure the easy passage of a suture. Prior to actuation, the surgeon threads the sutures between the spring and the central body. Subsequent to the passage of all necessary sutures through the suture-terminating device and once the surgeon is satisfied with the final position of the sutures, the removable members are withdrawn. The coaptation of the spring with the central body generates sufficient force on any sutures traversing the central body to restrict movement. Depending upon the desired result, the spring may be manufactured with sufficient force as to impede any movement of the suture.

In a preferred embodiment, the central body will have a sufficient number of flanges to form sufficient grooves for accommodating at lease two springs in a stacked orientation. In this embodiment, like the prior embodiment, the springs are maintained in their, pre-actuated, expanded state by removable members that are inserted between the springs and the central body through orifices on tabs which are located on the flanges. Subsequent to the passage of all necessary sutures through the suture-terminating device, the set of removable members are fractionally withdrawn, so that only the upper spring remains in its expanded state.

The lower spring, no longer impeded by the removable members contracts and coapts with the outer surface of the central body. The lower spring is preferably designed to exert sufficient force on the sutures as they traverse the device, to create sufficient tension to impede the sutures' easy movement without permanently locking them in place. This intermediate state provides the surgeon with the opportunity to adjust and readjust the position and tension on the sutures and to accurately position the prosthesis or tissue without breaking a suture. Once the surgeon is satisfied with the final position of the sutures, the device is actuated through the surgeon's full withdrawal of the removable members. This permits the upper spring to contract and to rest tightly on the outer surface of the central body within the groove formed by the flanges. The additional compression on the sutures by the upper spring locks the sutures in place and prevents their withdrawal from the suture-terminating device.

In still another preferred embodiment, the removable members are located on a deployment device that provides the surgeon with means for positioning and deploying the suture-terminating device under minimally imvasive conditions. The deployment device may be used in connection with suture-terminating devices having one or multiple springs.

In yet another preferred embodiment of the present invention, the suture-terminating device is made from biocompatible materials or biodegradable materials.

The present invention also contemplates the incorporation of at least one suture-terminating device, according to the present invention, incorporated within, and/or in physical contact with, a securable medical prosthesis. Such prosthesis include sewing ring implants shaped and sized for attachment to the inner surface of the native annulus of the heart.

The present invention also provides a method of using the suture-terminating device in connection with minimally invasive surgery.

The present invention is illustrated in terms of its preferred embodiments in the accompanying drawings.

BRIEF DESCRIPTION OF THE DRAWINGS

FIG. 2 is a bottom plan view of the suture-terminating device and the deployment device of FIG. 1;

FIGS. 3 and 4 are side views illustrating, respectively, the suture-terminating device and deployment device with a suture positioned in the device, in the pre-actuated and actuated positions;

FIG. 5 is a cross-sectional view along line 5—5 of the suture-terminating device of FIG. 2;

FIG. 6 is a side view of a central body of the suture-terminating device of FIG. 1;

FIG. 7 is a side view of a spring of the suture-terminating device of FIG. 1;

FIG. 8 is a top view of a spring of the suture-terminating device of FIG. 1;

FIG. 9 is a perspective view of an actuated suture-terminating device with sutures positioned in the device;

FIGS. 10 and 10a are sectional views illustrating, respectively, a suture in a pre-actuated and actuated suture-terminating device;

FIGS. 11 and 12 are close-up sectional views illustrating, respectively, the configuration of the deployment device and the suture-terminating device in the pre-actuated and actuated positions;

DESCRIPTION OF THE PREFERRED EMBODIMENTS

Figure 1:
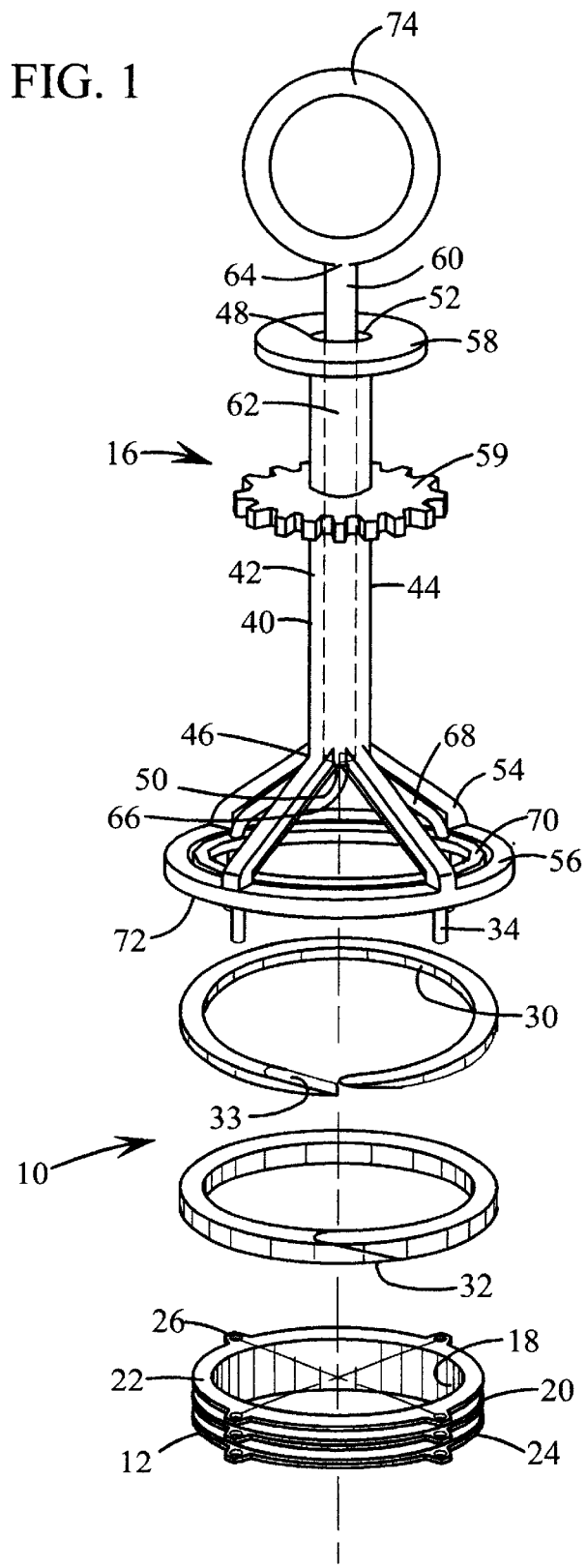
FIG. 1 is a perspective exploded view of a suture-terminating device and a deployment device both of the present invention.

The present invention terminates the ends of standard sutures without knots and without the need for manual proximity. Referring to FIG. 1, suture-terminating device 10 of the present invention comprises a central body 12 and at least one split ring spring 14.

Figure 13:
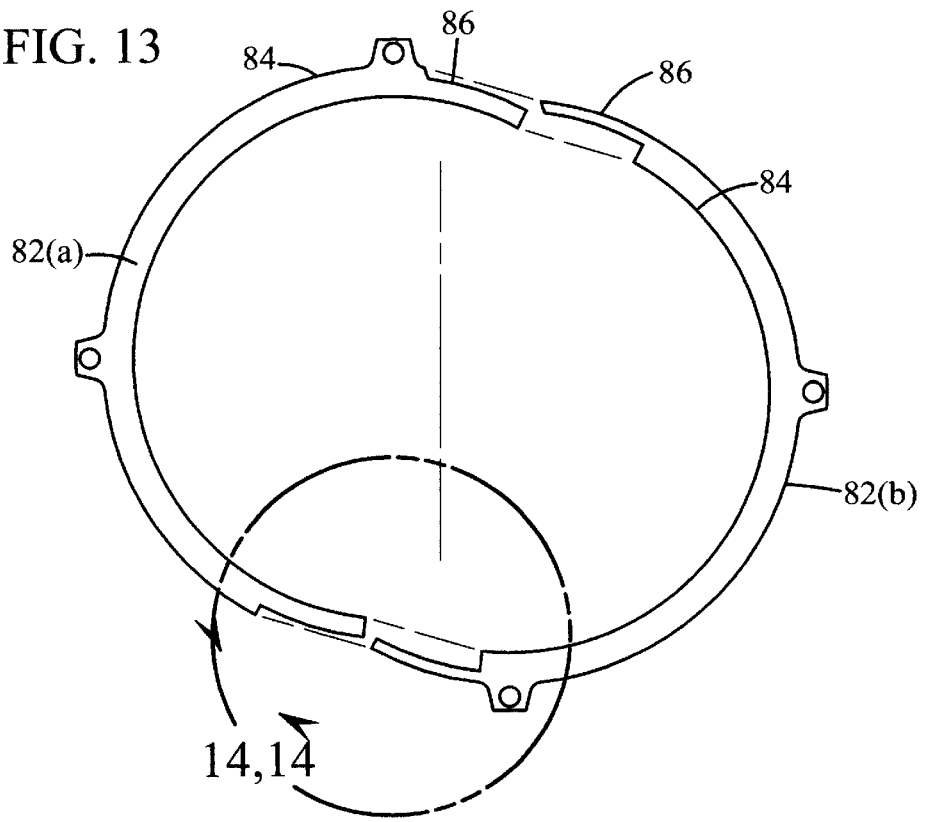
FIG. 13 is a top plan view of a second embodiment of the central body of the suture-terminating device of FIG. 1.
Figure 14:
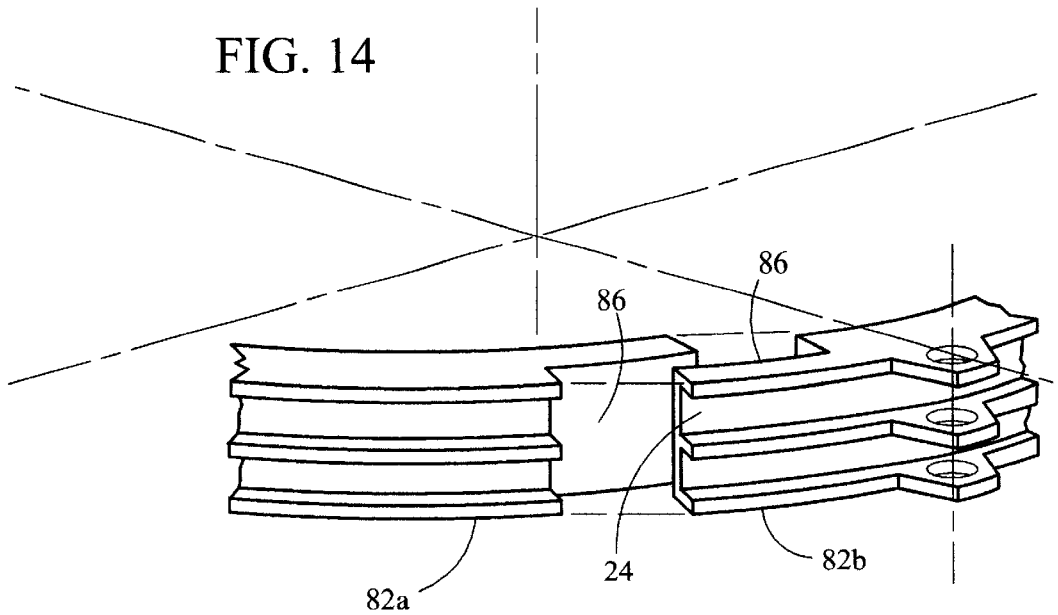
FIG. 14 is a close-up perspective view illustrating the mating components of the central body of FIG. 13 prior to coupling.

Under most circumstances, and as illustrated by FIG. 1, central body 12 will be constructed as a single unit. However, under certain circumstances (e.g. when used in connection with certain types of pre-existing prosthetic devices), it will be advantageous for central body 12 to be constructed, as depicted by FIG. 13, of at least two sections 82(a) and (b). Sections 82(a) and (b), as illustrated in FIGS. 13 and 15, are shaped to couple with each other, and to remain as a single unit, through the coaptation of central body 12 with springs 14, while suture-terminating device 10 is actuated.

The construction of central body 12 in sections facilitates the assembly of central body 12 around or within previously manufactured prosthetic devices. Sections 82(a) and (b) may, as illustrated by FIGS. 13–16, have a mirror image orientation to each other. When arranged in this configuration, the sections cooperate as pairs, each section receiving and coupling with the abutting mating components 86 of the other. While FIGS. 13–16 depict a frictional coupling arrangement, there are a number of additional means for attaching the sections including, the incorporation of dowels, latches, hooks, dove tails, or the like on the mating components. Sections 82 of central body 12 are coupled, once the surgeon is satisfied with the placement of sections 82 around or within the previously manufactured prosthetic device, through the application of force to the outer surface of walls 84. Following coupling, sections 82 exist as a single unit, through the coaptation of central body 12 with springs 14.

Figure 15:
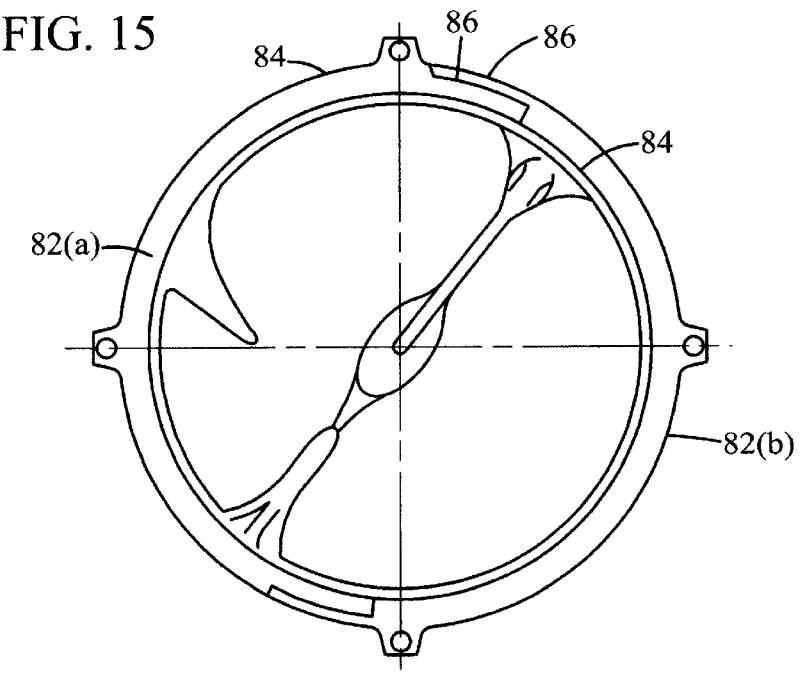
FIG. 15 is a top plan view of the second embodiment of the central body of FIG. 13 post coupling.
Figure 16:
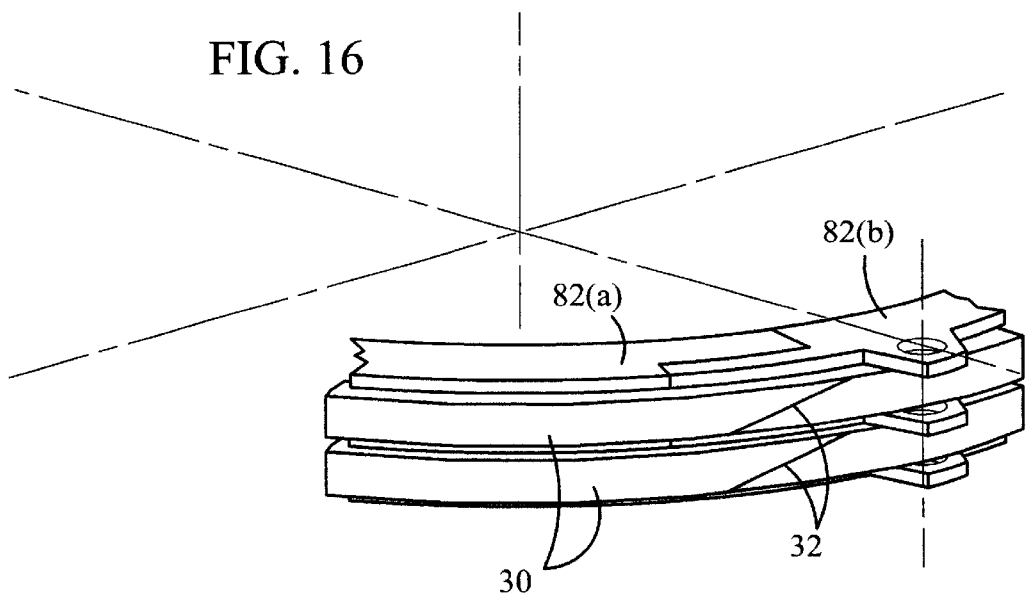
FIG. 16 is a close-up perspective view illustrating the mating components of the central body of FIG. 13 post coupling.
Figure 17:
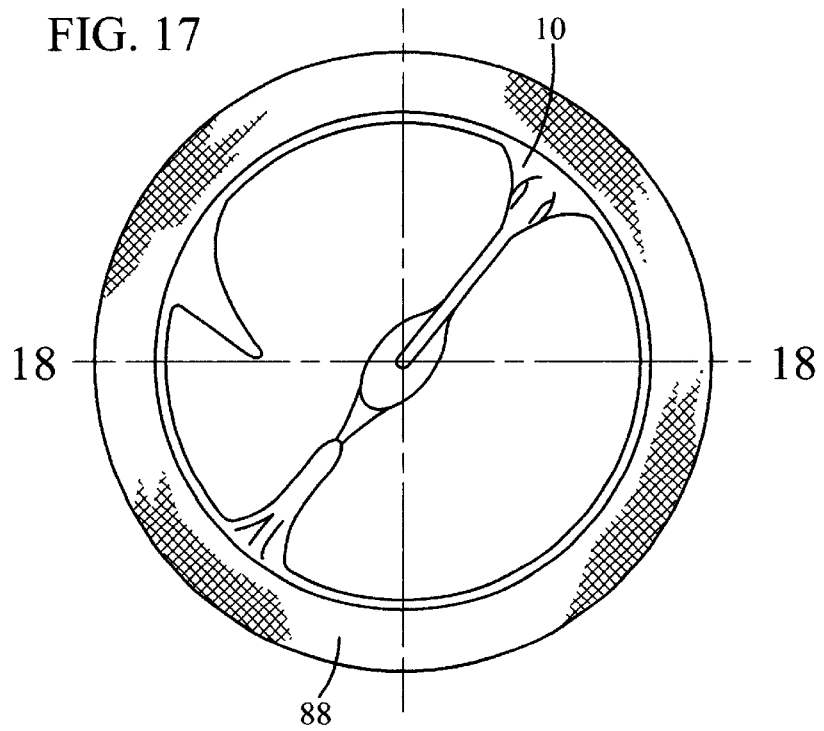
FIG. 17 is a top plan view of the suture-terminating device of the present invention embedded in an annuloplasty ring.
Figure 18:
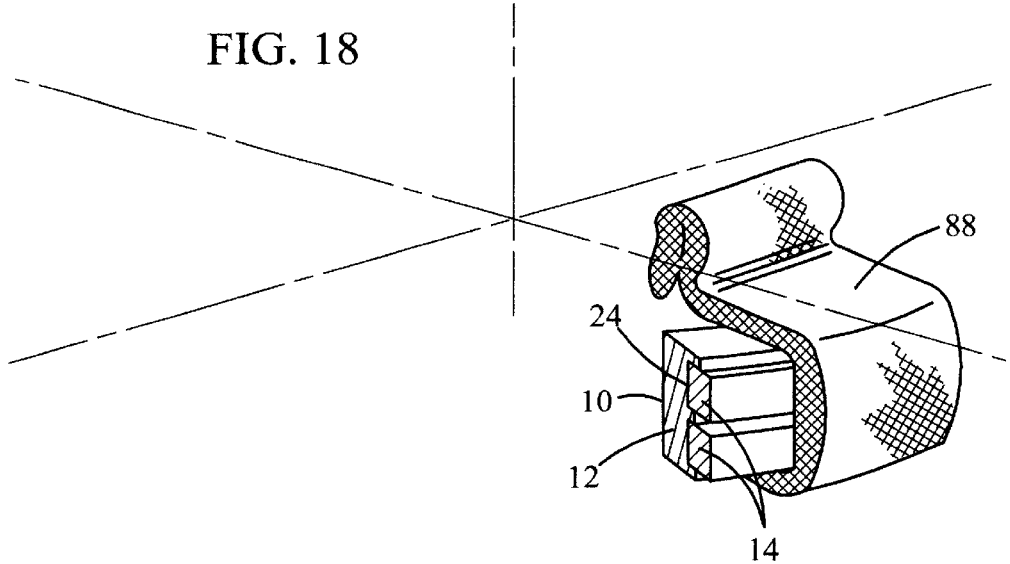
FIG. 18 is a cross-sectional view along line 18—18 of the suture-terminating device of FIG. 17.

Central body 12, may, as illustrated in FIGS. 1 and 15, exist as a free standing device or be incorporated into a prosthetic device such as an annuloplasty ring 88, as illustrated in FIGS. 17 and 18. Central body 12 may be constructed in a variety of manners including the milling or molding of biocompatible plastics and metals or biodegradable materials.

Depending upon the suture-terminating device's actual application, the size of the suture, and the material used, the size and shape of central body 12 may vary. However, central body 12 should, in all cases, be large enough to both contain and support a sufficient number of sutures drawn through the device, without disruption or distortion to the local native tissue and/or the prosthetic device or tissue attached thereto or thereby. For example, if central body 12 and springs 14 are constructed of stainless steel and are intended to be used with 2-0 braided synthetic suture material for securing a heart valve sewing ring, then central body 12 should be 0.045" (width) by 3.3" (length) by 0.057" (thickness) and springs 14 will either overlap or under-lap main member central body 12, while suture-terminating device 10 is in its pre-actuated state, by approximately 0.25" depending upon the configuration.

An additional benefit of the present invention is that, under certain circumstances, central body 12 also functions as a pledget (e.g. disbursing the pressure of the suture over a surface area greater than that of the suture alone, thus bolstering the suture's coupling of the desired members (e.g., tissue to native tissue and/or prosthetic to native tissue) while reducing the likelihood of damage to the prosthetic device or the surrounding tissue.

In a preferred embodiment of the present invention, central body 12 has an inner wall 18 and an outer surface 20. Extending radially from outer surface 20 are flanges 22. Flanges 22 and outer surface 20 form groove(s) 24. Outer surface 20 within groove(s) 24 may be smooth, may have at least one ridge, irregularities, or local deformations so as to enhance the frictional capability of holding a suture. Extending radially from flanges 22 are tabs 26 which, as more clearly depicted in FIG. 2, house orifices 28. Orifices 28 are axially aligned and cooperate to receive removable members 34.

In a preferred embodiment of the present invention, central body 12 cooperates with two springs 14. However, it is likely that the present invention may, depending upon the application, rely on the cooperation of only a single spring or more then two springs with the central body.

In the embodiment depicted in FIGS. 1–6, the central body 12 has three flanges that run latitudinally around the circumference of its outer surface 20. Flanges 22 (cooperate with outer surface 20 to form grooves 24 which are sized to fittedly accommodate springs 14. When actuated, springs 14 will be disposed within grooves 24 that are positioned on or about the equatorial plain of central body 12. Although, as discussed above, the number and position of these grooves may vary under certain circumstances, they will generally be, as illustrated in FIG. 6, latitudinally disposed and in a stacked configuration. When arranged in this configuration, the grooves cooperate as a pair, each groove receiving one of the springs.

Referring now to FIGS. 7 and 8, springs 14 are preferably a hardened surgical steel ring having an angular open slit 32 to allow radial distension under pressure. Inner surface 30 of springs 14 may be smooth, or possess irregularities, deformations, or at least one ridge, depending upon the device's application.

Returning to FIG. 2, gap 36 is created, when springs 14, in their expanded state, are symmetrically spaced from central body 12 by removable members 34. Gap 36, must be sized to permit the unobstructed passage of sutures. Once removable members 34 are withdrawn, the outer tapered surfaces 33 of slit 32 slide inward along each other, causing spring 14 to contract and grip tightly central body 12, which it surrounds. In turn, the force exerted by spring 14 on central body 12 is preferably sufficient to restrict movement on any sutures traversing the central body and springs though gap 36. Depending upon the desired result, springs 14 may be manufactured with sufficient force to fully impede or to simply restrict the sutures' movement.

In certain embodiments of the present invention, like the current embodiment, where it is preferable to have two springs working in tandem, it is desirable that spring 14(b) exert greater force than spring 14(a) at a ratio of two-to-one. Such a combination will enhance the surgeon's ability to adjust and readjust the position and tension on the sutures and to accurately position the prosthesis or tissue without breaking a suture.

In yet another preferred embodiment of the present invention (not depicted), the central body has at least two flanges running latitudinally around the circumference of its inner wall. In this embodiment, suture termination is accomplished, through the cooperation of the central body with at least one split ring compression spring. Prior to actuation, the spring is maintained in its compressed state by removable members that are inserted between the spring and the central body through orifices on tabs that are located on the flanges. Once actuated, the spring expands to rest tightly on the inner surface of the central body within the groove formed by the flanges.

In the present embodiment, like the above referenced embodiments, the removable members maintain sufficient space between the outer surface of the central body and the inner surface of the spring to ensure the easy passage of a suture. Prior to actuation, the surgeon threads the sutures through the gap, between the spring and central body, created by the removable members. Subsequent to the passage of all necessary sutures through the suture-terminating device and once the surgeon is satisfied with the final position of the sutures, the removable members are withdrawn. The coaptation of the spring with the central body generates sufficient force on any sutures traversing the central body to restrict movement. Depending upon the desired result, the spring may be manufactured to generate sufficient force as to inhibit or to fully restrict any movement of the suture.

In still another embodiment of the present invention, which will be more fully discussed below, deployment device 16 is utilized by the surgeon to position and actuate suture-terminating device 10. In this embodiment, orifices 28 of tabs 26 are positioned along flanges 22 to receive and cooperate with removable members 34 of deployment device 16. Actuation is accomplished through the withdrawal of removable members 34 from tabs 26. Once actuated, springs 14 contract to rest tightly on the outer surface 20 of central body 12 within grooves 24.

As previously discussed, prior to actuation, removable members 34 insure the maintenance of sufficient space between the outer surface 20 of central body 12 and the inner surface 30 of springs 14 to insure easy passage of a suture 8 through gap 36. While in its pre-actuated state, the surgeon attaches prosthesis or tissue to native tissue by threading sutures 8 through gap 36. Subsequent to the passage of all necessary sutures through the suture-terminating device 10, removable members 34 are fractionally withdrawn, so that only spring 14(b) remains in its expanded state. The lower spring 14(a) no longer impeded by removable members 34 contracts and coapts with the outer surface 20 of central body 12.

While in this intermediate state, lower spring 14(a) is, as provided above, preferably designed to exert sufficient force on sutures 8, as they traverse the device, to create sufficient tension to impede the sutures' easy movement without permanently locking them in place. This intermediate state provides the surgeon with the opportunity to adjust and readjust the position and tension on the sutures and to accurately position the prosthesis or tissue without breaking or damaging any of the sutures, the prosthesis or the tissue.

Once the surgeon is satisfied with the final position of the sutures, the suture-terminating device 10 is actuated through the surgeon's full withdrawal of the removable members 34. This full withdrawal permits upper spring 14(b) to contract and rest tightly on outer surface 20 of central body 12 within groove 24(b). The additional compression on the sutures 8 exerted by upper spring 14(b) locks the sutures in place and prevents their withdrawal from suture-terminating device 10.

In a second preferred embodiment of the present invention, deployment device 16 is utilized by the surgeon to position and actuate suture-terminating device 10. This embodiment is particularly useful in minimally invasive surgical procedures since it provides the surgeon with a means for easier access to tissue and organs that had traditionally been difficult to work on without disrupting the surrounding tissue. Depending upon the suture-terminating device's actual application and the materials used, the size and shape of deployment device 16 may vary. By way of example, when used during minimally invasive procedures in combination with a suture-terminating device embedded within a heart valve sewing ring, deployment device 16 must have sufficient length to permit the surgeon to manipulate and place the replacement valve in the desired portion of the patient's heart, from outside the patient, without requiring the surgeon to open the patient's chest cavity.

Returning to FIG. 1, deployment device 16 comprises tubular body 40 that houses hollow longitudinal passageway 42 which moves over and guides the movement of piston 60 within. Body 40 may be constructed in a variety of ways including the milling or molding of biocompatible plastics and metals. Body 40 is formed by at least one wall 44, which as presently depicted is generally tubular in nature, having a proximal end 46 and a distal end 48. Openings 50 and 52 are formed by wall 44 at the body's proximal and distal ends, respectively. Radiating from proximate end 46 is at least one strut 54 that fixedly connects spacing ring 56 to body 40. Removable members 34, which are received by and cooperate with tabs 26 of suture-terminating device 10, extend outward from spacing ring 56 in a proximal orientation. Extending radially from proximal end 46 is flange 58. Located on wall 44, between flange 58 and distal end 48 is suture guide 59. It is envisioned that flange 58 and suture guide 59 may in certain applications be combined or obviated entirely.

Piston 60, which travels longitudinally within passageway 42, may be constructed in a variety of ways including the milling or molding of biocompatible plastics and metals. Piston 60 comprises an elongated shaft 62 having a proximal end 64 and a distal end 66. Radiating from proximate end 64 is at least one strut 68 that fixedly connects deployment ring 70 to piston 60. Deployment ring 70 has a bottom surface 72 that remains in contact with the suture-terminating device until actuation has been completed. Deployment trigger 74 is positioned at the distal end of piston 60.

As FIGS. 11 and 12 illustrate, deployment device 16 is reversibly coupled to suture-terminating device 10 through the cooperation of the deployment device's removable members 34 and the suture-terminating device's orifices 28. Prior to actuation, removable members 34 are inserted fully within tabs 26. During actuation, withdrawal of removable members 34 is accomplished through the surgeon's compression of flange 58 towards trigger 74. In turn, removable members 34, which as discussed above extend from spacing ring 56, are withdrawn from orifices 28, since body 44 recedes over piston 60 pulling spacing ring 56 with it, in a distal direction, while deployment ring 70 prevents suture-terminating device 10 from moving. Fractional withdrawal may be accomplished in a number of ways including marking or grading piston 60 (not depicted). While suture-terminating device 10 is in its pre-actuated and intermediate states, suture guide 59 prevents the accidental tangling of sutures 8. Once actuation is completed, the surgeon cuts the remaining sutures and removes the deployment device from within the patient.

In still another preferred embodiment (not depicted), the deployment device is sized and shaped to facilitate suture termination under minimally invasive conditions. Specifically, the tubular body may be bent or curved. Under such circumstances, the piston is preferably constructed from a flexible substance to ensure easy passage of the piston through the tubular body. In addition, the tubular body may be constructed telescopically or from a flexible material, thus providing the surgeon with greater opportunity to maneuver and deploy the suture-terminating device under minimally invasive.

EXAMPLE 1

By way of example, this invention may be incorporated, as provided above, into heart valve prosthetics. As depicted in FIGS. 17 and 18, by incorporating the present invention into the sewing ring of a heart valve or heart annuloplasty ring 88 or device, the surgeon would merely have to feed sutures 8 through gap 36. The prosthesis would be positioned, and the sutures locked into place without the need for the proximity of manual knot tying.

Typically the surgeon would place double-ended sutures through the native annular tissue in a concentric fashion around the valve annulus. Each paired suture end would then be threaded through the appropriately paired knotless suture device. These devices will be incorporated into the perimeter of prosthetic valve sewing ring at appropriate distances depending upon the application. The valve is then advanced from outside the patient's body into the heart. The surgeon then removes all slack from the suture and places the valve in its desired position. Once positioned, removable members 34 are fractionally withdrawn. While in this intermediate state, the surgeon adjusts and readjusts the position and tension on the sutures and accurate positions the valve. Once the surgeon is satisfied with the final position of the sutures and the valve, suture-terminating device 10 is actuated through the surgeon's full withdrawal of removable members 34.

After verification of proper tension and valve position, the suture ends are cut off. This is particularly advantageous for use with minimally invasive techniques since, as discussed above, these apparatus and systems obviate the need for tying knots.

EXAMPLE 2

The present invention will also be useful for thoracoscopic thoracic surgery. It is necessary to place sutures to stop bleeding during thoracic surgery. This invention would allow standard suture technique to be use through thorascopic ports, without forcing proximity to the site of the suture in order to terminate the suture ends. In this application, a smaller version of this device would be incorporated in to felt pledged material. The ends of the placed sutures would be placed through gap 36. Piston 60 is used to lower the pledged device into apposition with the sutured tissue. When the suture had generated the appropriate tension, deployment flange 58 would be withdrawn against trigger 74, and the suture locking mechanism deployed. The surgeon would then cut the long ends of the suture material.

As is known in the art, all exposed parts of the invention should generally be made of biocompatible materials, either synthetic or natural, from which surgical implants are typically made, for example, polymers, plastics, biological tissue, metals and alloys, and combinations thereof. In addition, embodiments of this invention can be constructed of biodegradable materials.

As noted above, the Figures and Examples provided are intended to further describe the aspects of the present invention. Thus, the Figures and Examples are illustrative only and are not to be construed as limiting the scope of that which is regarded as the invention. Furthermore, while only two embodiments of the invention has been presented in detail in this disclosure, it will be apparent to those of skill in the art that many modifications, adaptations, and changes may be made thereto without departing from the spirit and scope of the invention. In short, the scope of the present invention is only to be limited by the following claims and the equivalents thereto.

What is claimed is:

1. A suture-terminating device comprising:
   (a) a central body having at least one surface;
   (b) a plurality of flanges extending radically outward from the surface and defining at least one groove there between, wherein the groove has a base wall and at least one side wall and each flange has at least one aperture axially aligned and spaced away from the base wall;
   (c) at least one removable member disposed within each aperture; and
   (d) at least one spring disposed adjacently to the surface, and maintained in its expanded state by contact with, the removable member disposed within the aperture, the spring positioned adjacent to and spaced from the base wall while in its expanded state, defining a gap of sufficient size to permit the passage of at least one suture there through, whereby withdrawal of the removable member from the aperture permits the spring to contract inwardly within the groove towards the base wall, and cooperate with the base wall and the side wall to restrict the suture's movement through the gap.

2. The suture-terminating device according to claim 1, wherein the central body is an integral unit.

3. The suture-terminating device according to claim 1, wherein the central body comprises a plurality of sections that are shaped to couple with each other to form a single unit when the suture-terminating device is actuated.

4. The suture-terminating device according to claim 3, wherein the plurality of sections comprising the central body are coupled by a coupling means selected from the group consisting of: frictional coupling means, dowels, latches, hooks, or dove tails.

5. The suture-terminating device according to claim 1, wherein the base wall of each groove is smooth.

6. The suture-terminating device according to claim 1, wherein the base wall of each groove is has at least one ridge, irregularity, or local deformation to enhance the frictional capability of holding a suture.

7. The suture-terminating device according to claim 1, wherein the device has two or more springs.

8. The suture-terminating device of claim 7, wherein the springs each exert identical degrees of force.

9. The suture-terminating device of claim 7, wherein at least two springs exert different degrees of force relative to each other.

10. The suture-terminating device according to claim 1, wherein the springs are hardened surgical steel.

11. The suture-terminating device according to claim 1, wherein the springs are annular.

12. The suture-terminating device according to claim 1, wherein the springs are disposed fully around the periphery of the base wall.

13. The suture-terminating device according to the claim 1, wherein the springs are disposed partially around the periphery of the base wall.

14. The suture-terminating device according to claim 1, wherein the springs have an angular open slit to allow radial distension under pressure.

15. The suture-terminating device according to claim 1, wherein the central body is annular.

16. The suture-terminating device according to claim 1, wherein at least one flange extends fully around the periphery of the central body.

17. The suture-terminating device according to claim 1, wherein at least one flange extends partially around the periphery of the central body.

18. The suture-terminating device according to claim 1, wherein the apertures are spaced away from the base wall on tabs extending radically from the flanges.

19. A prosthetic device comprising a suture-terminating device according to claim 1.

20. The suture-terminating device according to claim 1, wherein the removable member is a pin.

21. The suture-terminating device according to claim 1, wherein the removable member is attached to a deployment device.

22. The suture-terminating device according to claim 20, wherein the removable member is integral to the deployment device.

23. The suture-terminating device according to claim 20, wherein the deployment device comprises a longitudinal body of sufficient length to permit the surgeon to manipulate and deploy the suture-terminating device in the desired portion of a patient's body, from outside the patient, under minimally invasive conditions.

24. The deployment device according to claim 23, wherein the longitudinal body is graded to facilitate fractional withdrawal of the removable members from the suture-terminating device.

25. The deployment device according to claim 23, wherein the longitudinal body is straight.

26. The deployment device according to claim 23, wherein the longitudinal body is shaped to facilitate manipulation and deployment of the suture-terminating device under minimally invasive conditions.

27. The suture-terminating device according to claim 23, wherein the length of the longitudinal body is adjustable.

28. The suture-terminating device according to claim 1, wherein the suture-terminating device is made from biodegradable materials.

29. A kit comprising:
    (a) A suture-terminating device according to claim 1; and
    (b) Sutures of a desired gauge for use with the terminating device.

30. The kit according to claim 29, wherein the suture-terminating device is manufactured within a prosthetic device.

31. A method for terminating a suture near a suturing site, comprising the steps:
    (a) providing a suture, connected at a suturing site and having at least one free end;
    (b) providing a suture-terminating device comprising a central body having at least one surface, with a plurality of flanges extending from the surface and defining at least one groove therebetween, wherein each flange has at least one aperture axially aligned and spaced away from the base wall, with at least one spring disposed adjacently to and spaced from the surface, and maintained in its expanded state by contact with at least one removable member, defining a gap of sufficient size to permit the passage of at least one suture there through;
    (c) threading at least one free end of the suture through the gap;
    (d) sliding the suture-terminating device to a desired position adjacent to the suturing site; and
    (e) withdrawing the removable member, whereby the spring is permitted to contract inwardly and cooperate with the surface to restrict the suture movement through the gap.

* * * * *